United States Patent
Karanjgaokar

(10) Patent No.: US 9,409,849 B2
(45) Date of Patent: Aug. 9, 2016

(54) RECOVERY OF AROMATIC CARBOXYLIC ACIDS AND OXIDATION CATALYST

(75) Inventor: C. G. Karanjgaokar, Mumbai (IN)

(73) Assignee: Invista North America S.A.R.L., Wilmington, DE (US)

(*) Notice: Subject to any disclaimer, the term of this patent is extended or adjusted under 35 U.S.C. 154(b) by 0 days.

(21) Appl. No.: 13/637,460

(22) PCT Filed: Mar. 16, 2011

(86) PCT No.: PCT/US2011/028666
§ 371 (c)(1),
(2), (4) Date: Dec. 10, 2012

(87) PCT Pub. No.: WO2011/119395
PCT Pub. Date: Sep. 29, 2011

(65) Prior Publication Data
US 2013/0079551 A1    Mar. 28, 2013

(30) Foreign Application Priority Data
Mar. 26, 2010  (IN) .............................. 826/CHE/2010

(51) Int. Cl.
C07C 51/48    (2006.01)
C07C 51/265   (2006.01)
C22B 7/00     (2006.01)

(52) U.S. Cl.
CPC ............... *C07C 51/48* (2013.01); *C07C 51/265* (2013.01); *C22B 7/009* (2013.01); *Y02P 10/214* (2015.11)

(58) Field of Classification Search
None
See application file for complete search history.

(56) References Cited

U.S. PATENT DOCUMENTS

| | | |
|---|---|---|
| 3,341,470 A | 9/1967 | Hensley |
| 4,298,759 A | 11/1981 | Harper et al. |
| 4,459,365 A | 7/1984 | Suzuki et al. |
| 4,490,297 A | 12/1984 | Feld et al. |
| 4,910,175 A | 3/1990 | Michel et al. |
| 4,939,297 A * | 7/1990 | Browder et al. .............. 562/485 |
| 5,955,394 A | 9/1999 | Kelly |
| 6,001,763 A | 12/1999 | Feitler |
| 6,307,099 B1 | 10/2001 | Turner |
| 7,358,392 B2 | 4/2008 | Sheppard et al. |

FOREIGN PATENT DOCUMENTS

RU    2341512 C2    12/2008

* cited by examiner

*Primary Examiner* — Karl J Puttlitz
(74) *Attorney, Agent, or Firm* — Finnegan, Henderson, Farabow, Garrett & Dunner, LLP

(57) ABSTRACT

The present invention relates to a process for recovery of catalyst, aromatic polycarboxylic acids and aromatic monocarboxylic acids from a residue stream from manufacture of an aromatic polycarboxylic acid.

18 Claims, 1 Drawing Sheet

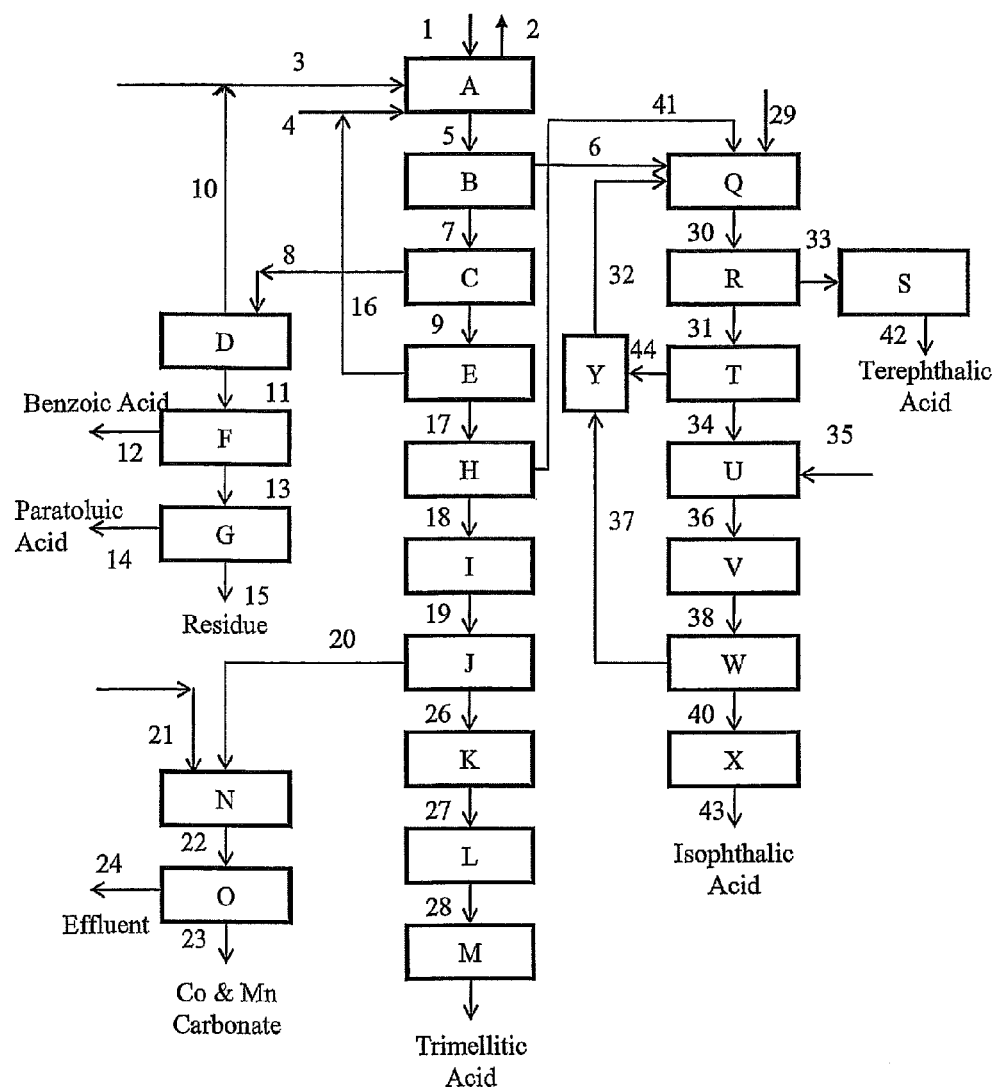

RECOVERY OF AROMATIC CARBOXYLIC ACIDS AND OXIDATION CATALYST

FIELD OF THE INVENTION

This invention relates to the recovery of aromatic carboxylic acid and oxidation catalyst from the effluent of a process for producing aromatic polycarboxylic acids by liquid phase oxidation of the corresponding aromatic precursor.

BACKGROUND OF THE INVENTION

Terephthalic acid is manufactured by liquid-phase oxidation of p-xylene with air using a cobalt-manganese-bromide catalyst system (cobalt acetate, manganese acetate and hydrogen bromide) in acetic acid in the temperature range from 150 to 230° C. The relative ratio of cobalt, manganese and bromine are important, and the typical values are manganese:cobalt ratio 1:1 and cobalt: bromine ratio 1:2. In the reactor and crystallizer, most of the terephthalic acid crystallizes out from the mother liquor and is separated by filtration. The mother liquor comprises mainly acetic acid and organic compounds, for example, isophthalic acid, benzoic acid, para toluic acid, trimellitic acid, and terephthalic acid, and inorganic compounds such as cobalt, manganese and bromine compounds along with iron, nickel, calcium, chromium and sodium. Typically, a large portion of the recovered mother liquor is recycled to the oxidation reaction in order to recycle catalyst components to the oxidation reaction while purging a smaller portion to a solvent recovery system so as to maintain the level of impurities and by-products in the reaction within tolerable limits. This is called the purge stream, which is a mixture of oxygen-containing derivatives of benzene and toluene which are mono-, di- and tricarboxylic acids, aldehydocarboxylic acids, and methylol-substituted benzene or toluene or their carboxylic (benzoic or toluic) acids and which also contains catalyst components.

In a solvent recovery step, the purge stream is subjected to evaporation to remove a considerable portion of the acetic acid and water leaving a concentrate containing organic compounds together with catalyst components. The concentrate leaving can then be incinerated or treated. While such residues amount to from 2 to 25 weight percent of the aromatic polycarboxylic acid produced, such residue production annually is substantial in view of the millions of kilograms of the aromatic polycarboxylic acids produced annually. Such residues contain water-soluble aromatic carboxylic acids and water-soluble forms of the catalyst compounds. Landfill disposal of such residues is undesirable because rain and groundwater leach out the carboxylic acids, and soluble forms of the catalyst components can contaminate surface run-off water, water ways, and below-surface aquifers. Therefore, processes have been developed to recover the valuable chemicals from the purge stream of the reactor effluent, but these processes are not optimal.

U.S. Pat. No. 3,341,470 discloses incinerating the residue to oxide ash and dissolving the ash with sulphuric acid containing chloride. The manganese and cobalt components are recovered by treatment of the solution with sodium carbonate to precipitate cobalt and manganese as their carbonates. The recovered carbonates are then treated with acetic acid to produce acetates for recycle to the oxidation reaction.

A method for recovery of cobalt and manganese from the reactor effluent is given by Dynamit Nobel AG. (U. S. Pat. No. 4,490,297). The catalysts are isolated in the form of oxalates from the mother liquor stream and cobalt oxalate dihydrate and/or manganese oxalate dihydrate are restored by the action of hydrogen bromide and acetic anhydride to a form in which they are soluble in acetic acid and can be used again. Similarly, U.S. Pat. No. 4,910,175 discloses recovery of cobalt and manganese catalyst from oxidation process, by precipitation with oxalic acid and alkali metal hydroxide, followed by oxidation of precipitate in acetic acid to form cobalt and manganese acetate.

U.S. Pat. No. 6,001,763 discloses a process for recovering a solution of cobalt and manganese acetates and other valuables components of a reactor effluent of used catalyst discharged from terephthalic acid manufacturing process. The residue is pyrolized in a reaction zone forming molten metal in an electric arc and converting essentially all carbon in the residue to oxides of carbon, hydrogen and compounds vaporized in an effluent from the reaction zone. The alloy recovered is atomized to form a metal powder which is then reacted with acetic acid and aqueous hydrogen bromide to form the corresponding salts.

SUMMARY OF THE INVENTION

Many of the above disclosed methods involve separation of catalyst in oxalate form followed by oxidation of the oxalate salt to acetate using acetic acid. These methods separate cobalt and manganese catalysts but in low yield and with a long cycle time. Also these methods cannot separate the aromatic carboxylic acids, bromide and acetic acid present in the residue. Therefore, there exists a need for a method of recovering aromatic carboxylic acids, bromide and acetic acid along with cobalt and manganese catalysts at high yields and reduced cycle times.

In accordance with the present invention, a method has been found to recover aromatic carboxylic acids, bromide and acetic acid along with cobalt and manganese catalysts at high yields and reduced cycle times. The present invention embodies a process comprising: (a) producing a residue stream from manufacture of an aromatic polycarboxylic acid; (b) separating the residue stream into a dicarboxylic acid rich stream, a catalyst and tricarboxylic acid rich stream, and a monocarboxylic acid rich stream; and (c) separating at least one aromatic polycarboxylic acid from the dicarboxlic acid rich stream.

In another embodiment, a process is disclosed comprising: (a) producing a residue stream from manufacture of an aromatic polycarboxylic acid; (b) separating the residue stream into a dicarboxylic acid rich stream, a catalyst and tricarboxylic acid rich stream, and a monocarboxylic acid rich stream; (c) separating at least one aromatic monocarboxylic acid from the monocarboxylic acid rich stream; (d) separating at least one aromatic dicarboxylic acid from the dicarboxylic acid rich stream; and (e) separating at least one catalyst component from the catalyst and tricarboxylic acid rich stream.

In a further embodiment, a process is disclosed comprising: (a) producing a residue stream from manufacture of terephthalic acid; (b) separating the residue stream into a dicarboxylic acid rich stream, a catalyst and tricarboxylic acid rich stream, and a monocarboxylic acid rich stream; (c) separating benzoic acid and paratoluic acid from the monocarboxylic acid rich stream; (d) separating terephthalic acid and isophthalic acid from the dicarboxylic acid rich stream; (e) separating trimellitic acid from the catalyst and tricarboxylic acid rich stream; and (f) separating a cobalt salt and manganese salt from the catalyst and tricarboxylic acid rich stream.

In yet another embodiment, a process is disclosed comprising: (a) producing a residue stream from manufacture of isophthalic acid; (b) separating the residue stream into a dicarboxylic acid rich stream, a catalyst and tricarboxylic acid rich stream; and a monocarboxylic acid rich stream; (c) separating benzoic acid and meta-toluic acid from the monocarboxylic acid rich stream; (d) separating terephthalic acid and isophthalic acid from the dicarboxylic acid rich stream; (e) separating trimellitic acid from the catalyst and tricarboxylic acid rich stream; and (f) separating a cobalt salt and manganese salt from the catalyst and tricarboxylic acid rich stream.

BRIEF DESCRIPTION OF THE DRAWINGS

FIG. 1 is a schematic representation of one embodiment of the inventive process for the recovery of chemicals and catalyst from the concentrated purge from the reactor exit solvent recovery section of a terephthalic acid manufacturing plant by a solvent extraction method, followed by concentration, evaporation and drying.

DETAILED DESCRIPTION OF THE INVENTION

The present invention can be characterized by a process comprising: (a) producing a residue stream from manufacture of an aromatic polycarboxylic acid; (b) separating the residue stream into a dicarboxylic acid rich stream, a catalyst and tricarboxylic acid rich stream, and a monocarboxylic acid rich stream; and (c) separating at least one aromatic polycarboxylic acid from the dicarboxlic acid rich stream. The aromatic polycarboxylic acid can comprise at least one member selected from the group consisting of terephthalic acid (TA), isophthalic acid (IPA), trimellitic acid (TMA), orthophthalic acid (OA), naphthalene dicarboxylic acids (NDA), other similar acids and anhydrides thereof, and mixtures thereof The catalyst can comprise at least one member selected from the group consisting of cobalt salt, manganese salt, hydrobromic acid, vanadium, chromium, iron, molybdenum, nickel, cerium, zirconium, hafnium and mixtures thereof The hydrobromic acid can be present as the sodium salt. The monocarboxylic acid can comprise at least one member selected from the group consisting of benzoic acid (BA), paratoluic acid (pTol) and its isomers and mixtures thereof The dicarboxylic acid can comprise at least one member selected from the group consisting of terephthalic acid (TA), isophthalic acid (IPA), naphthalene dicarboxylic acids (NDA) and mixtures thereof The tricarboxylic acid can comprise at least one member selected from the group consisting of trimellitic acid (TMA), hemi-mellitic acid, trimesic acid and mixtures thereof.

Another embodiment of the present invention is a process comprising: (a) producing a residue stream from manufacture of an aromatic polycarboxylic acid; (b) separating the residue stream into a dicarboxylic acid rich stream, a catalyst and tricarboxylic acid rich stream, and a monocarboxylic acid rich stream; (c) separating at least one aromatic monocarboxylic acid from the monocarboxylic acid rich stream; (d) separating at least one aromatic dicarboxylic acid from the dicarboxylic acid rich stream; and (e) separating at least one catalyst component from the catalyst and tricarboxylic acid rich stream. The aromatic polycarboxylic acid can comprise at least one member selected from the group consisting of terephthalic acid, isophthalic acid, trimellitic acid, orthophthalic acid, naphthalene dicarboxylic acids, other similar acids and anhydrides thereof, and mixtures thereof The aromatic monocarboxylic acid can comprise at least one member selected from the group consisting of benzoic acid (BA), paratoluic acid (pTol) and its isomers and mixtures thereof. The catalyst can comprise at least one member selected from the group consisting of cobalt salt, manganese salt, hydrobromic acid, vanadium, chromium, iron, molybdenum, nickel, cerium, zirconium, hafnium and mixtures thereof. The hydrobromic acid can be present as the sodium salt. The process can further comprise a step (d-i) separating trimellitic acid from the catalyst and tricarboxylic acid rich stream after step (d).

A further embodiment of the present invention is a process comprising: (a) producing a residue stream from manufacture of terephthalic acid; (b) separating the residue stream into a dicarboxylic acid rich stream, a catalyst and tricarboxylic acid rich stream, and a monocarboxylic acid rich stream; (c) separating benzoic acid and paratoluic acid from the monocarboxylic acid rich stream; (d) separating terephthalic acid and isophthalic acid from the dicarboxylic acid rich stream; (e) separating trimellitic acid from the catalyst and tricarboxylic acid rich stream; and (f) separating a mixture of cobalt salt and manganese salt from the catalyst and tricarboxylic acid rich stream. The resulting effluent from the catalyst recovery step (f) can be further subjected to recovery of hydrobromic acid by acidification of the effluent using a concentrated mineral acid such as sulphuric acid.

Yet another embodiment of the present invention is a process comprising: (a) producing a residue stream from manufacture of isophthalic acid; (b) separating the residue stream into a dicarboxylic acid rich stream, a catalyst and tricarboxylic acid rich stream; and a monocarboxylic acid rich stream; (c) separating benzoic acid and meta-toluic acid from the monocarboxylic acid rich stream; (d) separating terephthalic acid and isophthalic acid from the dicarboxylic acid rich stream; (e) separating trimellitic acid from the catalyst and tricarboxylic acid rich stream; and (f) separating a cobalt salt and manganese salt from the catalyst and tricarboxylic acid rich stream. The resulting effluent from the catalyst recovery step (f) can be further subjected to recovery of hydrobromic acid by acidification of the effluent using a concentrated mineral acid such as sulphuric acid.

In all of the above embodiments, the process can further comprise a step $(a_i)$ removing acetic acid from the residue stream after step (a). Also, in all of the above embodiments of the present invention, the separation process of step (b) can comprise an extraction followed by filtration. The extraction can comprise the use of water and an organic solvent comprising at least one member selected from the group consisting of toluene, methanol, cyclohexane, petroleum ether and mixtures thereof Also, in all of the above embodiments of the present invention, at least one of the separating steps can comprise i) optionally, adding an aqueous solution, ii) evaporating at least some water, iii) cooling, iv) filtering out a precipitate, and v) repeating steps ii) through iv) to produce a purified stream.

Another embodiment of the present invention is a process to recover components of a residue stream from manufacture of an aromatic polycarboxylic acid (i.e. Terephthalic Acid (TA) Oxidation Plant) comprising:
 1. Optionally, partially or fully removing acetic acid and traces of water from a residue stream under vacuum and the acetic acid can then be purified optionally by rectification.
 2. Stirring and heating the residue stream with toluene and water at from about 75° C. to 80° C. Water can be present as residual water in the residue stream. The two phase extract is filtered (producing a cake) and separated. The filtered toluene extract is sent for concentration and further isolation of crude benzoic acid and paratoluic acid in stages 4 and 5.

3. Sending the filtered water extract from step 2 for catalyst and trimellitic acid recovery in step 8, and sending the filter cake from step 2 for terephthalic acid/isophthalic acid recovery in step 6.
4. Pumping the toluene extract from step 2 to a solvent evaporation system. Here toluene is removed by evaporation, and all traces of toluene are removed under vacuum. The molten crude benzoic acid is sent to a benzoic distillation column.
5. Fractionating the crude benzoic acid from step 4 as the top product in the benzoic distillation column and the purified molten benzoic acid is sent to the flaker. Flaked pure benzoic acid can be sold. The bottom product from the benzoic acid distillation column is sent to the paratoluic distillation column to separate paratoluic acid and residual organics. Purified paratoluic acid is recovered as the top product from the paratoluic distillation column and can be recycled to the TA Oxidation Plant.
6. Extracting the filter cake from step 3 and step 8 with methanol and water at about 60° C. The extracted slurry is centrifuged or filtered to generate a terephthalic acid solid (containing from about 90-99% terephthalic acid and from about 1-10% isophthalic acid) which can be recycled to the TA Oxidation Plant.
7. Concentrating the filtrate/centrate from step 6 through evaporation, and then cooling, which causes isophthalic acid to precipitate. The resulting slurry is then centrifuged or filtered and dried. This generates an isophthalic acid solid containing from about 90-99% isophthalic acid and from about 1-10% terephthalic acid, which can be sold.
8. Concentrating the aqueous extract from step 3 by evaporation of water to about 20%-40% volume and hot filtering. The solids retained by the filter comprise terephthalic acid and isophthalic acid and this material is sent to terephthalic acid/isophthalic acid recovery (step 6). The filtrate is cooled and centrifuged or filtered. The solids cake contains crude trimellitic acid. This is then purified by re-dissolution in hot water, followed by cooling and centrifuging or filtration. The purified trimellitic acid can be dried and sold and 9. Reacting concentrated filtrate/centrate from step 8 with sodium carbonate to precipitate cobalt and manganese carbonate. This slurry is filtered, and the recovered cobalt and manganese carbonates are recycled to the TA Oxidation Plant. The filtered mother liquor can be sent for effluent treatment.

A further embodiment of the present invention is a process to recover components of a residue stream from manufacture of a terephthalic acid (TA Oxidation Plant) comprising:

1. Optionally, partially or fully evaporating acetic acid and traces of water from a terephthalic acid plant residue stream optionally under vacuum and the acetic acid can then be purified optionally by rectification.
2. Stirring and heating the residue stream with toluene and water at from about 75° C. to 80° C. The two phase extract is filtered (producing a cake) and separated. The filtered toluene extract is sent for concentration and further isolation of crude benzoic acid and paratoluic acid in steps 4 and 5.
3. Sending the filtered water extract from step 2 for catalyst and trimellitic acid recovery in step 9, and sending the filter cake from step 2 for terephthalic acid/isophthalic acid recovery in step 6.
4. Pumping the toluene extract from step 2 to a solvent evaporation system. Here toluene is removed by evaporation, and all traces of toluene are removed under vacuum. The molten crude benzoic acid is sent to a benzoic distillation column in step 5.
5. Fractionating crude benzoic acid from step 4 as the top product in the benzoic distillation column and the purified molten benzoic acid is sent to the flaker. Flaked pure benzoic acid can be sold. The bottom product from the benzoic acid distillation column is sent to the paratoluic distillation column to separate paratoluic acid and residual organics. Purified paratoluic acid is recovered as the top product from the distillation column and can be recycled to the TA Oxidation Plant.
6. Dissolving filter cake from step 3 and step 9 in an aqueous ammonia solution (typically from about 10-30%, including from about 20-30%) at a temperature of from about 20-50° C. The resulting solution is filtered to remove any insoluble catalyst present in the residues. This is particularly effective to remove catalyst metal oxalates which can be present in the residue stream. These catalyst metal oxalates can either be recycled to the TA Oxidation Plant, or converted to catalyst metal acetate by an appropriate route.
7. Reacting the filtered solution from step 6 with a dilute mineral acid such as nitric, sulphuric or hydrochloric acid to reduce the pH in a two stage process. The pH is reduced to the range from about 4-4.5, which causes terephthalic acid to precipitate. This solid which contains from about 90-95% terephthalic acid and 5-10% isophthalic acid is separated from the solution. The resulting solids are then washed with water and can be recycled to the TA Oxidation Plant.
8. Reacting the mother liquor from step 7 with mineral acid to reduce the pH to the range from about 2.7-3, which causes isophthalic acid to precipitate. These solids, which contain from about 91-92% isophthalic acid and from about 8-9% terephthalic acid, are separated from the solution, washed with water, dried and can be sold. Mother liquor from step 8 can either be disposed of in a biological effluent treatment plant, or can be further reacted with mineral acid to precipitate benzoic acid and trimellitic acid if required.
9. Concentrating the aqueous extract from step 3 by evaporation of water to about 20% volume and hot filtering. The solids retained by the filter comprise terephthalic acid and isophthalic acid and this material is sent to terephthalic acid/isophthalic acid recovery (step 6). The filtrate is cooled, precipitating more solids that are separated. The solids cake contains crude trimellitic acid. This is then purified by re-dissolution in hot water, followed by cooling, precipitating and separating. The purified trimellitic acid can be dried and sold.

and

10. Reacting concentrated mother liquor from step 9 with sodium carbonate to precipitate cobalt and manganese carbonate. This slurry is filtered, and the recovered cobalt and manganese carbonates are recycled to the TA Oxidation Plant. The filtered mother liquor can be sent for effluent treatment.

Yet another embodiment of the present invention is a process to recover components of a residue stream from manufacture of a terephthalic acid (TA Oxidation Plant) comprising:

1. Optionally, partially or fully evaporating acetic acid and traces of water from a terephthalic acid plant residue stream optionally under vacuum and the acetic acid can then be purified optionally by rectification.
2. Stirring and heating the residue stream with toluene and water at from about 75° C. to 80° C. Water can be present as residual water in the residues stream. The two phase extract is filtered (producing a cake) and separated. The filtered toluene extract is sent for concentration and further isolation of crude benzoic acid and paratoluic acid in stages 4 and 5.
3. Sending the filtered water extract from step 2 for catalyst and trimellitic acid recovery in step 8 and sending the filter cake from step 2 for terephthalic acid/isophthalic acid recovery in step 6.
4. Pumping the toluene extract from step 2 to a solvent evaporation system. Here toluene is removed by evaporation, and all traces of toluene are removed under vacuum. The molten crude benzoic acid is sent to a benzoic distillation column.
5. Fractionating crude benzoic acid from step 4 as the top product in the benzoic distillation column and the purified molten benzoic acid is sent to the flaker. Flaked pure benzoic acid can be sold. The bottom product from the benzoic acid distillation column is sent to the paratoluic distillation column to separate paratoluic acid and residual organics. Purified paratoluic acid is recovered as the top product from the distillation column and can be recycled to the TA Oxidation Plant.
6. Extracting filter cake from step 3 and step 8 with methanol and water at about 60° C. The slurry is centrifuged or filtered to generate a terephthalic acid solid (containing from about 90-99% terephthalic acid and from about 1-10% isophthalic acid) which can be recycled to the TA Oxidation Plant.
7. Concentrating centrate/filtrate from step 6 through evaporation, and then cooling, which causes isophthalic acid to precipitate. The resulting slurry is then centrifuged or filtered and dried. This generates an isophthalic acid solid containing from about 90-99% isophthalic acid and from about 1-10% terephthalic acid, which can be sold.
8. Concentrating the aqueous extract from step 3 by evaporation of water to about 40% volume and hot filtering. The solids retained by the filter comprise terephthalic acid and isophthalic acid and this material is sent to terephthalic acid/isophthalic acid recovery (step 6). The filtrate is cooled to from about 30-40° C. and precipitated solids separated. The solids cake contains crude trimellitic acid. The mother liquor is further evaporated, reducing its volume by 50%, and then cooled to from about 30-40° C. and precipitated solids separated again. The combined crude trimellitic acid solids from the two stages of separation containing from about 70-75% trimellitic acid are then fed to the trimellitic acid purification stage (step 9).
9. Washing crude trimellitic acid with hot acetic acid solvent (containing from about 90-95% acetic and from about 5-10% water) at a temperature of from about 90-100° C. The washed cake is then filtered from the acetic acid, and filtered cake is then washed with water to displace any acetic acid. The washed solid is then dried, and then sold or converted into trimellitic anhydride.
10. Cooling and filtering the acetic acid solvent filtrate from step 9, causing orthophthalic acid to precipitate. The solids are then filtered and removed from the process. The filtered acetic acid solvent can be recycled to the TA Oxidation Plant.
and
11. Reacting the combined mother liquors from step 8, together with aqueous wash liquor from step 9 with sodium carbonate to precipitate cobalt and manganese carbonate. The slurry is filtered, and the recovered cobalt and manganese carbonates are recycled to the TA Oxidation Plant. The filtered mother liquor can be sent for effluent treatment.

Yet a further embodiment of the present invention is a process to recover components of a residue stream from manufacture of an isophthalic acid comprising:
1. Optionally, fully or partially evaporating acetic acid and traces of water from an isophthalic acid plant residue stream optionally under vacuum and the acetic acid can then be purified optionally by rectification.
2. Stirring and heating the residue stream with a mixture of about 50% methanol and about 50% water at a temperature in the range from about 50° C. to 80° C. The extract is filtered (producing a cake) and separated. The filtered extract is sent for solvent evaporation and further solvent extraction in step 3.
3. Pumping the extract from step 2 to a solvent evaporation system. Here the methanol/water solvent is removed by evaporation. The solid is then extracted with toluene and water, and resulting two phase mixture is filtered, and then separated by phase separation in a decanter to generate two liquid phases.
4. Pumping the toluene extract from step 3 to a solvent evaporation system. Here toluene is removed by evaporation, and all traces of toluene are removed under vacuum. The molten crude benzoic acid is sent to a benzoic distillation column.
5. Fractionating crude benzoic acid from step 4 as the top product in the benzoic distillation column and sending the purified molten benzoic acid to the flaker. Flaked pure benzoic acid can be sold. The bottom product from the benzoic acid distillation column is sent to the meta-toluic acid distillation column to separate toluic acid and residual organics. Purified meta-toluic acid is recovered as the top product from the meta-toluic distillation column and can be recycled to the isophthalic acid oxidation plant.
6. Dissolving filter cake from step 2 and step 9 in a aqueous ammonia solution (typically from about 10-30%, including from about 20-30%) at a temperature of from about 20-50° C. The resulting solution is filtered to remove any insoluble catalyst which is present in the residues.
7. Reacting the filtered solution from step 6 with a dilute mineral acid such as nitric, sulphuric or hydrochloric acid to reduce the pH in a two stage process. The pH is reduced to the range from about 4-4.5, which causes terephthalic acid to precipitate. This solid which contains from about 90-95% terephthalic acid and from about 5-10% isophthalic acid is separated from the solution. The resulting solids are then washed with water and can be bagged for external sale.
8. Reacting mother liquor from step 7 with mineral acid to reduce the pH to the range from about 2.7-3, which causes isophthalic acid to precipitate. These solids, which contains from about 91-92% isophthalic acid, and from about 8-9% terephthalic acid, are separated from the solution, and then washed with water and recycled to the isopthalic acid oxidation plant. Mother liquor from step 8 can either be disposed of in a biological effluent treatment plant, or can be further reacted with mineral acid to precipitate benzoic acid and trimellitic acid if required.
9. Concentrating aqueous extract from step 3 by evaporation of water to about 20%-40% volume and hot filtering. The solids retained by the filter comprise terephthalic acid and isophthalic acid and this material is sent to terephthalic acid/isophthalic acid recovery (step 6). The filtrate is cooled and precipitated solids separated. The solids cake contains crude trimellitic acid. This is then purified by re-dissolution in hot water, followed by cooling and centrifuging. The purified trimellitic acid can be dried and bagged for sale.

and

10. Reacting concentrated mother liquor from step 9 with sodium carbonate to precipitate cobalt and manganese carbonate. This slurry is filtered, and the recovered cobalt and manganese carbonates are recycled to the isophthalic acid oxidation plant. The filtered mother liquor can be sent for effluent treatment.

Even yet another embodiment of the present invention is a process to recover components of a residue stream from manufacture of an isophthalic acid comprising:

1. Optionally, fully or partially evaporating acetic acid and traces of water from an isophthalic acid plant residue stream optionally under vacuum, and the acetic acid can then be purified optionally by rectification.
2. Stirring and heating the residue stream with toluene and water at from about 75° C. to 80° C. Water can be present as residual water in the residues stream. The two phase extract is filtered (producing a cake) and separated. The filtered toluene extract is sent for concentration and further isolation of crude benzoic acid and metatoluic acid in steps 4 and 5.
3. Sending the filtered water extract from step 2 for catalyst and trimellitic acid recovery in step 8 and sending the filter cake from step 2 for terephthalic acid/isophthalic acid recovery in step 6.
4. Pumping the toluene extract from step 2 to a solvent evaporation system. Here toluene is removed by evaporation, and all traces of toluene are removed under vacuum. The molten crude benzoic acid is sent to a benzoic distillation column.
5. Fractionating crude benzoic acid from step 4 as the top product in the benzoic distillation column and the purified molten benzoic acid is sent to the flaker. Flaked pure benzoic acid can be sold. The bottom product from the benzoic acid distillation column is sent to the metatoluic distillation column to separate metatoluic acid and residual organics. Purified metatoluic acid is recovered as the top product from the metatoluic distillation column and can be recycled to the IPA Oxidation Plant.
6. Extracting filter cake from step 3 and step 8 with methanol and water at about 60° C. The slurry is centrifuged/filtered to generate a terephthalic acid solid (containing from about 90-99% terephthalic acid and from about 1-10% isophthalic acid) which can be dried and bagged for sale.
7. Concentrating the centrate or filtrate from step 6 through evaporation, and then cooling, which causes isophthalic acid to precipitate. The resulting slurry is then separated and dried. This generates an isophthalic acid solid containing from about 90-99% isophthalic acid and from about 1-10% terephthalic acid, which can be recycled to the isophthalic acid oxidation plant.
8. Concentrating the aqueous extract from step 3 by evaporation of water to about 40%-60% volume and filtered hot filtering. The solids retained by the filter comprise terephthalic acid and isophthalic acid and this material is sent to terephthalic acid/isophthalic acid recovery (step 6). The filtrate is cooled to from about 30-40° C. and precipitated solids separated. The solids cake contains crude trimellitic acid. The mother liquor is further evaporated, reducing its volume by 50%, and then cooled to from about 30-40° C. and precipitated solids separated again. The combined crude trimellitic acid solids from the two stages of separation containing around from about 70-75% trimellitic acid are then fed to the trimellitic acid purification step (step 9).
9. Washing crude trimellitic acid with hot acetic acid solvent (containing from about 90-95% acetic and from about 5-10% water) at a temperature of from about 90-100° C. The washed cake is then filtered from the acetic acid, and filtered cake is then washed with water to displace any acetic acid. The washed solid is then dried, and can be sold or converted into anhydride.
10. Cooling and filtering the acetic acid solvent filtrate from step 9, causing orthophthalic acid to precipitate. This material is then filtered and removed from the process. The filtered acetic acid solvent can be recycled to the isophthalic acid oxidation plant.

and

11. Reacting concentrated mother liquor from step 8 together with aqueous wash liquor from step 9 with sodium carbonate to precipitate cobalt and manganese carbonate. This slurry is filtered, and the recovered cobalt and manganese carbonates are recycled to the isophthalic acid oxidation plant. The filtered mother liquor can be sent for effluent treatment.

Yet even a further embodiment of the present invention is a process to recover components of a residue stream from manufacture of an isophthalic acid comprising:

1. Optionally, fully or partially evaporating acetic acid and traces of water from an isophthalic acid plant residue stream optionally under vacuum, and the acetic acid can then be purified optionally by rectification.
2. Stirring and heating the residue stream with toluene and water at from about 75° C. to 80° C. Water can be present as residual water in the residues stream. The two phase extract is filtered (producing a cake) and separated. The filtered toluene extract is sent for concentration and further isolation of crude benzoic acid and metatoluic acid in steps 4 and 5.
3. Sending the filtered water extract from step 2 for catalyst and trimellitic acid recovery in step 9 and sending the filter cake from step 2 for terephthalic acid/isophthalic acid recovery in step 6.
4. Pumping the toluene extract from step 2 to a solvent evaporation system. Here toluene is removed by evaporation, and all traces of toluene are removed under vacuum. The molten crude benzoic acid is sent to a benzoic distillation column.
5. Fractionating crude benzoic acid from step 4 as the top product in the benzoic distillation column and sending the purified molten benzoic acid to the flaker. Flaked pure benzoic acid can be sold. The bottom product from the benzoic acid distillation column is sent to the metatoluic distillation column to separate metatoluic acid and residual organics. Purified metatoluic acid is recovered as the top product from the metatoluic distillation column and can be recycled to the Isophthalic Acid Oxidation Plant.
6. Dissolving filter cake from step 3 and step 9 in a aqueous ammonia solution (typically from about 10-30%, including from about 20-30%) at a temperature of from about 20-50° C. The resulting solution is filtered to remove any insoluble catalyst which is present in the residues.
7. Reacting the filtered solution from step 6 with a dilute mineral acid such as nitric, sulphuric or hydrochloric acid to reduce the pH in a two stage process. Firstly the pH is reduced to the range from about 4-4.5, which causes terephthalic acid to precipitate. This solid, which contains from about 90-95% terephthalic acid and from about 5-10% isophthalic acid is separated from the solution. The resulting solids are then washed with water and can be bagged for external sale.

8. Reacting mother liquor from step 7 with mineral acid to reduce the pH to the range from about 2.7-3, which causes isophthalic acid to precipitate. The solids, which contain from about 91-92% isophthalic acid, and from about 8-9% terephthalic acid, are separated from the solution. The solids are then washed with water and recycled to the isophthalic acid oxidation plant; Mother liquor from step 8 can either be disposed of in a biological effluent treatment plant, or can be further reacted with mineral acid to precipitate benzoic acid and trimellitic acid if required.

9. Concentrating the aqueous extract from step 3 by evaporation of water to about 40%-60% volume and filtered hot. The solids retained by the filter comprise terephthalic acid and isophthalic acid and this material is sent to terephthalic acid/isophthalic acid recovery (step 6). The filtrate is cooled to from about 30-40° C. and precipitated solids separated. The solids cake contains crude trimellitic acid. The mother liquor is further evaporated, reducing its volume by 50%, and then cooled to from about 30-40° C. and precipitated solids separated again. The combined crude trimellitic acid solids from the two stages of separation, containing from about 70-75% trimellitic acid are then fed to the trimellitic acid purification stage (step 10).

10. Washing crude trimellitic acid with hot acetic acid solvent (containing from about 90-95% acetic and from about 5-10% water) at a temperature of from about 90-100° C. The washed cake is then filtered from the acetic acid, and filtered cake is then washed with water to displace any acetic acid. The washed solid is then dried, and can be sold or converted into anhydride.

11. Cooling the acetic acid solvent filtrate from step 10, causing orthophthalic acid to precipitate. This solids are then filtered and removed from the process. The filtered acetic acid solvent can be recycled to the isophthalic acid oxidation plant.

and

12. Reacting concentrated mother liquor from step 9 together with aqueous wash liquor from step 10 with sodium carbonate to precipitate cobalt and manganese carbonate. This slurry is filtered, and the recovered cobalt and manganese carbonates are recycled to the isophthalic acid oxidation plant. The filtered mother liquor can be sent for effluent treatment.

In yet another embodiment of the present invention is a process to recover components of a residue stream from manufacture of a terephthalic acid (TA Oxidation Plant) comprising:

1. Optionally, fully or partially evaporating acetic acid and traces of water from a terephthalic acid plant residue stream optionally under vacuum and the acetic acid can then be purified optionally by rectification.

2. Stirring and heating the residue stream with toluene and water at from about 75° C. to 80° C. The two phase extract is filtered (producing a cake) and separated. The filtered toluene extract is sent for concentration and further isolation of crude benzoic acid and paratoluic acid in steps 4 and 5.

3. Sending the filtered water extract from step 2 for catalyst and trimellitic acid recovery in step 9 and sending the filter cake from step 2 for terephthalic acid/isophthalic acid recovery in step 6.

4. Pumping the toluene extract from step 2 to a solvent evaporation system. Here toluene is removed by evaporation, and all traces of toluene are removed under vacuum. The molten crude benzoic acid is sent to a benzoic distillation column in step 5.

5. Fractionating crude benzoic acid from step 4 as the top product in the benzoic distillation column and sending the purified molten benzoic acid to the flaker. Flaked pure benzoic acid can be sold. The bottom product from the benzoic acid distillation column is sent to the paratoluic distillation column to separate paratoluic acid and residual organics. Purified paratoluic acid is recovered as the top product from the paratoluic distillation column and can be recycled to the TA Oxidation Plant.

6. Dissolving filter cake from step 3 and step 9 in an aqueous ammonia solution (typically from about 10-30%, including from about 20-30%) at a temperature of from about 20-50° C. The resulting solution is filtered to remove any insoluble catalyst which is present in the residues. This is particularly effective to remove catalyst metal oxalates which may be present in the residue stream. These catalyst metal oxalates can either be recycled to the oxidation plant, or converted to catalyst metal acetate by an appropriate route.

7. Reacting the filtered solution from step 6 with a dilute mineral acid such as nitric, sulphuric or hydrochloric acid to reduce the pH in a two stage process. The pH is reduced to the range from about 4-4.5, which causes terephthalic acid to precipitate; These solids, which contains about from about 90-95% terephthalic acid and from about 5-10% isophthalic acid, is separated from the solution. The resulting solids are then washed with water and can be recycled to the TA oxidation plant.

8. Reacting mother liquor from step 7 with mineral acid to reduce the pH to the range from about 2.7-3, which causes isophthalic acid to precipitate. These solids, which contain from about 91-92% isophthalic acid and from about 8-9% terephthalic acid, are separated from the solution. The solids are then washed with water, dried and can be sold. Mother liquor from step 8 can either be disposed of in a biological effluent treatment plant, or can be further reacted with mineral acid to precipitate benzoic acid and trimellitic acid if required.

9. Concentrating the aqueous extract from step 3 by evaporation of water to about 40%-60% volume and hot filtering. The solids retained by the filter comprise terephthalic acid and isophthalic acid and this material is sent to terephthalic acid/isophthalic acid recovery (step 6). The filtrate is cooled to from about 30-40° C. and precipitated solids separated. The solids cake contains crude trimellitic acid. The mother liquor is further evaporated, reducing its volume by 50%, and then cooled to from about 30-40° C. and precipitated solids separated again. The combined crude trimellitic acid solids from the two stages of separation, containing from about 70-75% trimellitic acid are then fed to the trimellitic acid purification step (step 10).

10. Washing crude trimellitic acid with hot acetic acid solvent (containing from about 90-95% acetic and from about 5-10% water) at a temperature of from about 90-100° C. The washed cake is then filtered from the acetic acid, and filtered cake is then washed with water to displace any acetic acid. The washed solid is then dried, and can be sold or converted into trimellitic anhydride.

11. Cooling the acetic acid solvent filtrate from step 10, causing orthophthalic acid to precipitate. The solids are then filtered and removed from the process. The filtered acetic acid solvent can be recycled to the TA oxidation plant.

and

12. Reacting the combined mother liquor from step 9 together with aqueous wash liquor from step 10 with sodium carbonate to precipitate cobalt and manganese carbonate. The slurry is filtered, and the recovered cobalt and manganese carbonates are recycled to the TA Oxidation Plant. The filtered mother liquor can be sent for effluent treatment.

In yet even a further embodiment of the present invention is a process comprising:

1. Producing a residue stream from manufacture of terephthalic acid.
2. Evaporating acetic acid and traces of water from the residue stream under vacuum or at atmospheric pressure, such that acetic acid is recovered and recycled to the TA oxidation plant. The vacuum ranges from 5 mm Hg to 200 mm Hg.
3. Mixing the residue stream with a mixture of an organic solvent and water at a temperature of from about 35° C. to 100° C., including from about 60° C. to 90° C. and from about 75° C. to 80° C. The organic solvent can suitably comprise benzene, toluene, cyclohexane, methanol, petroleum ether or mixtures thereof. Suitably, the ratio for residue to organic solvent to water is in the range from 0.5-1:0.7 to 2:1-5. The slurry is filtered, producing a cake comprising unextracted insoluble material and the filtrate is separated into two liquid phases. The filtered organic extract is rich in monocarboxylic acids, and is sent for concentration and further isolation of crude benzoic acid and paratoluic acid in steps 5 and 6.

Further, the filtration process can be undertaken using a device such as, but not limited to a conventional bag or cartridge filter, membrane filters, agitated nutch filter, rotary vacuum filter, rotary pressure filter, or any other solid liquid separation device.
4. Sending the filtered water extract from step 3, which is rich in tricarboxylic acids and catalyst components, for catalyst and trimellitic acid recovery in step 9. Sending the filter cake of insoluble unextractable material from step 3, which is rich in dicarboxylic acids, for recovery of terephthalic acid and isophthalic acid in steps 7 and 8.
5. Transferring the organic extract from step 3 to the solvent evaporation system. Here the organic solvent is removed by evaporation, and residual traces of solvent are removed under vacuum. The resulting molten crude benzoic acid is sent to a benzoic distillation column.
6. Fractionating crude benzoic acid from step 5 as the top product in the benzoic distillation column and sending the purified molten benzoic acid to a flaker device. Flaked pure benzoic acid can be sold. The bottom product from the benzoic acid distillation column is sent to the paratoluic distillation column to separate paratoluic acid and residual organics. Purified paratoluic acid is recovered as the top product from the distillation column and can be recycled to the TA oxidation plant or can be sold.

The benzoic acid fractional distillation column can operate under vacuum at a pressure of from about 2 mmHg to about 760 mmHg, including from about 5-60 mmHg and from about 5-10 mmHg.

The paratoluic acid fractional distillation column can operate under vacuum at a pressure of from about 2 mmHg to about 760 mmHg, including from about 5-60 mmHg and from about 5-10 mmHg.

The bottoms product from the paratoluic acid column comprises a range of aromatic compounds which are not readily recovered or separated. This stream can be disposed of by any suitable means including biological digestion, landfill, and incineration or mixing with fuel for firing in furnace or boilers.
7. Extracting filter cake from step 3 with a secondary solvent comprising methanol, dimethyl formamide and water or mixtures thereof, at temperature in the range from about 30° C. -80° C., for example from about 50° C. -60° C. The slurry resulting from the extraction is separated using a filter or centrifuge to generate a terephthalic acid rich solid containing in the range from about 90-99.9% terephthalic acid, and from about 0.1-10% isophthalic acid, which is suitable for recycling to the TA oxidation plant, or can be dried for external sale. The composition of the solvent used in the above extraction can vary within the range of from about 10% concentration to about 90% concentration of either methanol or dimethyl formamide, or a mixture thereof, with the balance being water.

Further, the filtration can be undertaken in a device such as but not limited to a centrifuge, conventional bag or cathidge filter, membrane filters, agitated nutch filter, rotary vacuum filter, rotary pressure filter, or any other solid liquid separation device.

Also, the drying process can be undertaken using a device such as but not limited to spray dryers, rotary steam tube dryers, porcupine dryers, rotocone dryers or any other solvent removing device.

An alternative embodiment is obtained by varying the temperature and composition of the extraction solvent and a mixed product can be obtained comprising from about 50-90% terephthalic acid and from about 10-50% isophthalic acid. The mixed product can be filtered or centrifuged, and then dried, such a mixture being particularly suited to production of polyester polymers.
8. Concentrating mother liquor from the separation stage in step 7 through evaporation, and cooling. This causes isophthalic acid to precipitate. The resulting slurry is then filtered or centrifuged using any of the devices mentioned under step 7 and dried using any of the devices mentioned under step 7. In the course of filtering the isophthalic acid, the filter cake may be washed with solvent to further purify the isophthalic acid.

The resulting isophthalic acid solid contains about from about 90-99% isophthalic acid and from about 1-10% terephthalic acid, and can be sold, and can be used in the production of certain grades of polyester polymers.

The solvent which is evaporated in steps 7 and 8 can be purified by any known means, but preferably by fractional distillation, and can be recycled.
9. Concentrating the filtered aqueous extract from step 3 by evaporation to from about 20%-60% of the aqueous solvent and is filtered at a temperature in the range from about 50° C.-100° C., including from about 85° C.-95° C. The solids retained by the filter comprises mainly terephthalic acid and isophthalic acid and this material is transferred to terephthalic acid/isophthalic acid recovery (steps 7 and 8). The filtrate is cooled to a temperature in the range from about 20° C. -45° C. and as a result trimellitic acid crystallizes. The crude trimellitic acid slurry is filtered or centrifuged generating a cake containing crude trimellitic acid. This is then purified by re-dissolution in hot water, followed by cooling to re-crystallise the trimellitic acid, which is the separated from the water by filtration or centrifuging, and the resulting cake is dried. The purified trimellitic acid can be packaged for sale. Alternatively trimellitic acid can be converted to the anhydride by application of high temperature distillation, and the resulting anhydride can be flaked for external sale.

The aqueous solvent evaporated from any part of this step can be condensed and re-used in step 3 or elsewhere in the process.

and

10. Reacting concentrated mother liquor from step 9 with sodium carbonate, oxalic acid or tartaric acid or any other precipitating agent to convert the catalyst metal to insoluble form such as carbonates or oxalates or tartarates. For example, if sodium carbonate is added to precipitate cobalt and manganese carbonate, it is done so at a pH in the range from about 7.5-10. The resulting slurry of insoluble catalyst is filtered, the recovered insoluble catalyst metal salts can be washed to remove residual organic acids, and are then recycled to the upstream TA oxidation plant. Alternatively, the catalyst metals can be dried using any type of drying device, for merchant sale.

The filtered mother liquor can be sent for biological effluent treatment. Alternatively the filtered mother liquor can be processed to recover sodium bromide or hydrobromic acid by acidification using sulphuric acid or other concentrated mineral acids.

In recovering the insoluble catalyst metal salts, any type of solid-liquid separation device may be used including centrifuges, conventional bag or cartridge filter, membrane filters, agitated nutsch filter, rotary vacuum filter, rotary pressure filter or any other filtration device.

Another embodiment of the present invention can be characterized by a process to recover components of a residue stream from manufacture of an aromatic polycarboxylic acid (i.e. TA Oxidation Plant) comprising the following steps:

(i) Collecting the residue is in a vessel under vacuum to remove the trace acetic acid and recycle to the oxidation process. The vacuum ranges from about 5 mm Hg to 200 mm Hg.

(ii) Subjecting the residue to solvent extraction by solvents such as benzene, toluene, cyclohexane, methanol, petroleum ether and water in known ratios. The ratio for residue to organic solvent to water is in the range from about 0.5-1:0.7 to 2:1-5 and the extraction is carried out at a temperature in the range of from about 40° C. to 100° C.

(iii) Filtering the said content on a filter to give cake rich in terephthalic acid and isophthalic acid and filtrate rich in benzoic acid, paratoluic acid, cobalt, manganese, bromide, and trimellitic acid. The filtration can be carried out using a device such as, but not limited to a conventional bag or cartridge filter, membrane filter, agitated nutsch filter, rotary vacuum filter, rotary pressure filter, or any other solid liquid separation device.

(iv) Washing the filter cake from step (iii) with solvent, such as, methanol, dimethyl formamide, water, or mixtures thereof, or acetic acid, to give a cake rich in terephthalic acid and a filtrate rich in isophthalic acid. The filtration can be carried out in a device such as, but not limited to, a centrifuge, conventional bag or cartridge filter, membrane filter, agitated nutch filter, rotary vacuum filter, rotary pressure filter, or any other solid liquid separation device. The washing and filtration is carried out at a temperature in the range from about 50° C. to 90° C.

(v) Drying the cake from step (iv) to get a purified terephthalic acid. The drying process can be carried out using a device such as, but not limited to, spray dryers, rotary steam dryers, rotocone dryers or any other solvent removing device.

(vi) Subjecting the filtrate from step (iv) to concentration and solvent recovery for recycle. The concentrator can be of any type of evaporation device or distillation device or any other solid concentration device.

(vii) Rewashing the concentrated mass of step (vi) with a solvent such as methanol, dimethyl formamide, water or mixtures thereof, or acetic acid. The strength of the solvent can vary from the range of about 10% concentration to about 90% concentration with the balance being water.

(viii) Concentrating, filtering and drying the mass in step (vii), to recover pure isophthalic acid. The concentrator can be any type of evaporation or distillation device. Preferably the filtration can be carried out using a device such as, but not limited to, a conventional bag or cartridge filter, membrane filter, agitated nutch filter, rotary vacuum filter, rotary pressure filter, centrifuge or any other solid liquid separation device. Suitably, the dryer can be a device such as, but not limited to, spray dryers, rotary steam dryers, rotocone dryers or any other solvent removing device.

(ix) Recycling the filtrate coming out of step (viii) for its reuse as recycle solvent.

(x) Collecting the filtrate from step (iii) in a collection vessel and allowing sufficient time for separation of the organic and aqueous phases.

(xi) Collecting the organic layer from step (x) and subjecting it to concentration by evaporation to recover and reuse the solvent. The solvent recovery is achieved in any type of evaporation device or distillation device or any other solid concentration device.

(xii) Fractionating the bottoms from step (xi) by distillation and recovering the pure benzoic acid as a tops product. The fractionation is carried out in the temperature range of from about 100° C. to 150° C.

(xiii) Distilling the bottom product from step (xii) to recover para toluic acid. The distillation is carried out in the temperature range of from about 120° C. to 180° C.

(xiv) Treating the residue from step (xiii) by biological digestion, landfill, incineration or mixing with fuel for firing in furnace or boilers or any other suitable means.

(xv) Collecting the aqueous layer from step (x) and subjecting it to concentration for solvent recovery and reuse of solvent. The solvent recovery is carried out in any type of evaporation device or distillation device or any other solid concentration device.

(xvi) Cooling the concentrate, precipitating solids and then filtering the solids to get a cake rich in trimellitic acid and filtrate rich in cobalt, manganese and bromide. Filtration can be carried out using a device such as, but not limited to, conventional bag or cartridge filter, membrane filter, agitated nutch filter, rotary vacuum filter, rotary pressure filter, or any other solid liquid separation device.

(xvii) Treating the cake from step (xvi) and subjecting it to further purification by re-slurrying or re-crystallization and solid liquid separation. The device employed can be any type of solid liquid separation device. The product separated is trimellitic acid which is dried in a drier. The type of dryer can be a device such as, but not limited to, spray dryers, rotary steam dryers, rotocone dryers or any other solvent removing device.

(xviii) Precipitating the filtrate from step (xvi) which is rich in cobalt and manganese by reaction with sodium carbonate, oxalic acid, tartaric acid or any other agent to convert the heavy metal into an insoluble form, such as acetate, carbonate, oxalate, tartrate or other precipitate.

and (xix) Filtering the precipitate from step (xviii) to separate the cobalt and manganese salts as a cake which can be recycled to the TA oxidation plant or can be treated further to convert the metal salts into an alternative form (e.g. carbonates to acetates) and then sent to the TA oxidation plant or dried and sold. Drying can be carried out using spray dryers, rotary steam dryers, rotocone dryers or any other drying device.

The bromide coming out in the filtrate can either be sent to effluent for treatment or go to a bromine recovery unit. However, in step (xviii) if acetic acid is used, the entire content can be recycled to the TA oxidation plant with bromine recycle along with cobalt and manganese.

The aromatic carboxylic acid production processes in which the instant invention can be applicable are those processes employed on a commercial scale for production of terephthalic acid, isophthalic acid, orthophthalic acid and trimellitic acid, in which the aliphatic carboxylic acid solvent can be acetic acid.

The present invention may be better understood by reference to FIG. 1 which represents an embodiment of the present invention for the recovery of chemicals and catalyst from terephthalic acid manufacture.

Referring to FIG. 1, pipeline 1 is the inlet for the residue. The residue enters the collection vessel 'A' which is optionally subjected to acetic acid removal via pipeline 2. Pipeline 3 and 4 are for charging the organic and aqueous solvents respectively. Pipeline 5 feeds the contents in vessel 'A' to the filtration unit 'B'

Filtrate from 'B' goes to separation vessel 'C' via pipeline 7 for organic and aqueous layer separation. Pipeline 8 takes the organic layer to solvent recovery section 'D' and pipeline 9 routes the aqueous layer to concentrator 'E'.

Organic solvent is recovered in 'D' and routed back to the process by pipeline 10. The bottoms from 'D' are fed to the fractionation unit 'F' by pipeline 11. The top product from the fractionation unit 'F' is recovered via pipeline 12 this is benzoic acid. The bottoms from the fractionation unit 'F' are fed to another distillation tower 'G' by pipeline 13 for the purification and recovery of paratoluic acid. The purified paratoluic acid is recovered via stream 14 and the bottom product (residue) is sent for disposal via pipeline 15.

The aqueous solvent is recycled from concentrator 'E' to the feed line 4 as recovered solvent via pipeline 16. The concentrated bottoms from 'E' are filtered in filter 'H' via feed line 17. The cake from filter 'H' is rich in terephthalic and isophthalic acid and is recycled back for terephthalic and isophthalic acid recovery in Q via pipeline 41.

The filtrate is fed to cooler 'I' via feed line 18. Cooler exit is filtered on filter 'J' through feed line 19. The cake from exit filter 'J' is fed via pipeline 26 in crystallizer 'K'. The crystals from 'K', via line 27 are filtered on filter 'L' to isolate trimellitic acid, which is transferred via pipeline 28 to drier 'M' for recovery of the dry trimellitic acid product.

The filtrate from filter 'J' is collected in vessel 'N' via pipeline 20. This filtrate is precipitated by adding either oxalic acid or sodium carbonate via feed line 21. The precipitated cobalt and manganese mixture is fed to filter 'O' via pipeline 22. The cake from filter 'O' is recycled to TA Oxidation Plant by pipeline 23. The filtrate from 'O' is sent via pipeline 24 to the effluent treatment plant for disposal.

The cake from filter 'B' is collected in extraction vessel 'Q' via pipeline 6 and the cake from filter 'H' is collected in extraction vessel 'Q' via pipeline 41. Pipeline 29 feeds another solvent into the extraction vessel 'Q' for the extraction of terephthalic and isophthalic acid.

The material from extraction is fed to filter 'R' via pipeline 30. The cake comes out of pipeline 33 and is dried in dryer 'S' to give terephthalic acid product via pipeline 42 which can be recycled to the TA Oxidation Plant or as product for sale.

The filtrate from 'R' goes via pipeline 31 to solvent vaporiser 'T'. The evaporated solvent is fed by pipeline 44 to solvent processing unit 'Y' from where it is recycled to 'Q' via pipeline 32. The cake coming from pipeline 34 is washed in vessel 'U' with another solvent coming from pipeline 35. This mass is then fed via pipeline 36 to cooler 'V' where a slurry of isophthalic acid is formed.

The isophthalic acid slurry coming out from 'V' is fed via pipeline 38 to filter 'W'. Solvent from 'W' is recycled to solvent recovery unit 'Y' via pipeline 37 and isophthalic acid cake is fed to dryer 'X' via pipeline 40.

The dryer product coming out of 'X' is Isophthalic Acid and can be transferred as product for sale via pipeline 43.

Typically, in all the above embodiments, when the manufactured aromatic polycarboxylic acid comprises terephthalic acid, the residue stream comprises from about 2 to 25 weight percent acetic acid, from about 10 to 50 weight percent water, from about 50 to 60 weight percent organic components (mainly benzoic acid at from about 20 to 40 weight percent, isophthalic acid at from about 5-20 weight percent, and o-phthalic acid at from about 4 to 5 weight percent), and catalyst components comprising from about 0.2 to 1.5 weight percent of cobalt, from about 0.2 to 2 weight percent of manganese, and from about 2 to 5 weight percent of hydrobromic acid or the sodium salt thereof. It is understood that the specific residue will vary with the feeds and the process conditions and the process of this invention is no way limited by this particular composition of the reactor effluent.

While the invention has been described in conjunction with specific embodiments thereof, it is evident that many alternatives, modifications, and variations will be apparent to those skilled in the art in light of the foregoing description. Accordingly, the invention is intended to embrace all such alternatives, modifications and variations as fall within the spirit and scope of the claims.

What is claimed is:

1. A process comprising:
    (a) producing a residue stream from manufacture of an aromatic polycarboxylic acid;
    (b) separating the residue stream into a solid aromatic dicarboxylic acid rich stream, an aqueous stream rich in catalyst metal, acetic acid and aromatic tricarboxylic acid, and an organic stream rich in an aromatic monocarboxylic acid using a solvent extraction and
    (c) separating at least one aromatic polycarboxylic acid from the dicarboxylic acid rich stream
    wherein the separation process in step (b) comprises simultaneous extraction of the residue stream with two liquid phases, followed by filtration,
    wherein the simultaneous extraction of residue comprises the use of water and an organic solvent comprising at least one member selected from the group consisting of toluene, benzene, cylcohexane, petroleum ether, methanol and mixtures thereof.

2. The process of claim 1 wherein the aromatic polycarboxylic acid comprises at least one member selected from the group consisting of terephthalic acid, isophthalic acid, orthophthalic acid, trimellitic acid, naphthalene dicarboxylic acid and mixtures thereof.

3. The process of claim 2 wherein the catalyst components present in the catalyst and tricarboxylic acid rich stream comprise at least one member selected from the group consisting of a cobalt salt, a manganese salt, and mixtures thereof.

4. The process of claim 2 further comprising step ($a_i$) removing acetic acid by evaporation from the residue stream after step (a).

5. A process comprising:
(a) producing a residue stream from manufacture of an aromatic polycarboxylic acid;
(b) separating the residue stream into a solid aromatic dicarboxylic acid rich stream, an aqueous stream rich in catalyst metal, acetic acid and aromatic tricarboxylic acid, and an organic stream rich in an aromatic monocarboxylic acid using a solvent extraction;
(c) separating at least one aromatic monocarboxylic acid from the monocarboxylic acid rich stream;
(d) separating at least one aromatic dicarboxylic acid from the dicarboxylic acid rich stream; and
(e) separating at least one catalyst from the catalyst and tricarboxylic acid rich stream
wherein the separation process in step (b) comprises simultaneous extraction of the residue stream with two liquid phases, followed by filtration,
wherein the simultaneous extraction of residue comprises the use of water and an organic solvent comprising at least one member selected from the group consisting of toluene, benzene, cyclohexane, petroleum ether, methanol and mixtures thereof.

6. The process of claim 5 wherein the aromatic polycarboxylic acid comprises at least one member selected from the group consisting of terephthalic acid, isophthalic acid, orthophthalic acid, trimellitic acid, naphthalene dicarboxylic acid and mixtures thereof.

7. The process of claim 6 wherein the aromatic monocarboxylic acid comprises at least one member selected from the group consisting of benzoic acid, paratoluic acid and its isomers, and mixtures thereof.

8. The process of claim 6 wherein the catalyst comprises at least one member selected from the group consisting of a cobalt salt, a manganese salt, and mixtures thereof.

9. The process of claim 6 further comprising step ($d_i$) separating trimellitic acid or its isomers from the catalyst and tricarboxylic acid rich stream after step (d).

10. The process of claim 5 further comprising step ($a_i$) removing acetic acid from the residue stream by evaporation after step (a).

11. A process comprising:
(a) producing a residue stream from manufacture of terephthalic acid;
(b) separating the residue stream into a solid aromatic dicarboxylic acid rich stream, an aqueous stream rich in catalyst metal, acetic acid and aromatic tricarboxylic acid, and an organic stream rich in an aromatic monocarboxylic acid using a solvent extraction;
(c) separating benzoic acid and paratoluic acid from the monocarboxylic acid rich stream;
(d) separating terephthalic acid and isophthalic acid from the dicarboxylic acid rich stream;
(e) separating trimellitic acid from the catalyst and tricarboxylic acid rich stream; and
(f) separating a cobalt salt and manganese salt from the catalyst and tricarboxylic acid rich stream
wherein the separation process in step (b) comprises simultaneous extraction of the residue stream with two liquid phases, followed by filtration,
wherein the simultaneous two phase extraction of residue comprises the use of water and an organic solvent comprising at least one member selected from the group consisting of toluene, benzene, cyclohexane, petroleum ether, methanol and mixtures thereof.

12. The process of claim 11 further comprising step ($a_i$) removing acetic acid from the residue stream after step (a).

13. The process of claim 11 wherein the resulting effluent from the catalyst recovery step (f) is further subjected to recovery of hydrobromic acid by acidification of the effluent using a concentrated mineral acid such as sulphuric acid.

14. The process of claim 11 wherein the separating of step (d) comprises use of an alkali selected from the group consisting of aqueous ammonia, sodium hydroxide, and potassium hydroxide.

15. The process of claim 11 wherein the separating of step (d) comprises use of a solvent, wherein isophthalic acid is soluble in the solvent and terephthalic acid is insoluble in the solvent.

16. The process of claim 11, wherein at least one separating step comprises i) optionally, adding an aqueous solution, ii) evaporating at least some water, iii) cooling, iv) filtering out a precipitate, and v) repeating steps ii) through iv) to produce a purified stream.

17. The process of claim 16, wherein the precipitate of step iv) comprises crude tricarboxylic acid and the crude tricarboxylic acid is further purified by adding water, evaporating at least some of the water, and cooling to produce a crystallized further purified tricarboxylic acid.

18. The process of claim 16, wherein the precipitate of step iv) comprises crude tricarboxylic acid and the crude tricarboxylic acid is further purified by washing with a mixture of acetic acid and water, and then washing with water, to produce a further purified tricarboxylic acid.

* * * * *